(12) United States Patent
Klesse et al.

(10) Patent No.: US 6,194,530 B1
(45) Date of Patent: Feb. 27, 2001

(54) POLYMERS WITH ANTI-MICROBIAL PROPERTIES

(75) Inventors: Wolfgang Klesse, Mainz; Martina Pfirmann, Griesheim; Frank Hill, deceased, late of Mettmann, all of (DE), Hella Hill, legal representative

(73) Assignee: Roehm GmbH, Darmstadt (DE)

( * ) Notice: Subject to any disclaimer, the term of this patent is extended or adjusted under 35 U.S.C. 154(b) by 0 days.

(21) Appl. No.: 09/308,130

(22) PCT Filed: Oct. 21, 1997

(86) PCT No.: PCT/EP97/05806

§ 371 Date: Jul. 16, 1999

§ 102(e) Date: Jul. 16, 1999

(87) PCT Pub. No.: WO98/21253

PCT Pub. Date: May 22, 1998

(30) Foreign Application Priority Data

Nov. 14, 1996 (DE) ................................ 196 46 965

(51) Int. Cl.$^7$ .................................................. C08F 126/00
(52) U.S. Cl. ................. 526/312; 526/320; 526/328.5; 526/329.6; 526/332
(58) Field of Search ................... 526/312, 320, 526/328.5, 329.6, 332

(56) References Cited

U.S. PATENT DOCUMENTS

| | | | |
|---|---|---|---|
| 4,824,867 | * | 4/1989 | Smith et al. ................ 514/642 |
| 5,300,287 | * | 4/1994 | Park .......................... 424/78.04 |
| 5,408,022 | * | 4/1995 | Imazato et al. ............. 526/259 |
| 5,476,913 | * | 12/1995 | Kourai et al. ............... 526/310 |

FOREIGN PATENT DOCUMENTS 0 525 751 * 2/1993 (EP).
9112282 * 8/1991 (WO).

* cited by examiner

*Primary Examiner*—Helen L. Pezzuto
(74) *Attorney, Agent, or Firm*—Oblon, Spivak, McClelland, Maier & Neustadt, P.C.

(57) ABSTRACT

The invention relates to polymers with antimicrobial properties, consisting of: a) 99–40 wt % non functional vinylically polymerizable monomers and b) 1–60 wt % functional vinylically polymerizable monomers of general formula (I) wherein V=vinyl, (meth)acroyl, allyl or styryl, A=a possibly available linking unit, which can be alkyl, aryl, arylalkyl or hydroxy alkyl, which can also be interrupted by hetero atoms, e.g. by hetero atoms in urethane, carbonate, ester, amide or ether groups, wherein y=0 or is 1, Hsp=a hydrophilic spacer of general formula (i) —$(O-CH_2-CH_2)_r$— and/or (ii) —$(O-CH_2-CH(CH_3))_s$ with r=0–40, s=0–40 and r+s=2–40, also m=1.2 or 3 and $R^1=CH_3$, ethyl or benzyl, $R^2$=an alkyl radical with 8–20 C-atoms, wherein t=1, 2 or 3 and $X^-=Cl^-$, $Br^-$, $I^-$ or alkyl sulphate.

13 Claims, No Drawings

POLYMERS WITH ANTI-MICROBIAL PROPERTIES

The invention relates to polymers with antimicrobial properties. The polymers according to the invention comprise vinyl-type polymerizable monomers which are known themselves as well as monomers in which at least one long-chain alkyl residue is bonded to a quaternary ammonium group, which in turn is bonded with a vinyl function via a hydrophilic spacer and if applicable a linking unit.

PRIOR ART

European Patent Application 0641805 A1 describes polymers with antimicrobial (biophobic) properties. The polymers comprise ethylene-type unsaturated monomers containing some antimicrobial phenolic agents bonded covalently via side groups.

By analogy with polymers, the phenolic agents are bonded to repeat units having functional groups that can react with amino or hydroxyl groups. Examples of reactive residues are hydroxy, hydroxyalkyl, dialkylaminoalkyl or haloalkyl groups. The phenolic residues of the monomers having biocidal function are therefore bonded with the polymer matrix via relatively short, hydrophobic spacers.

The abstract of Japanese Patent 62-05936 (Chemical Abstracts, 107, 41977v) describes antifungal and antibacterial agents. These have a (meth)acryl residue, to which there is bonded a fluorinated aromatic group via an ethylene glycol, propylene glycol or hydroxypropylene group containing 1 to 4 units. The monomers, in the form of a polyvinyl chloride paste, are used, for example, as antimicrobial coating on paper. Use in polymers is not mentioned.

Nazarova et al. (Chemical Abstracts 122: 230183d: Khim.-Farm. Zh. (1993), 27 (2), 30-3) describe biophobic polymers of N-(2-hydroxypropyl)methacrylamide containing bound chloramphenicol.

Therein higher activity is observed in vivo when the chloramphenicol is additionally bonded to the polymer and cleaved from the polymer via a glycine-leucine-glycine spacer. The authors suspect particularly good action toward intracellular microorganisms. Obviously the ease of cleavage of the chloramphenicol from the polymer by enzymatic hydrolysis of the peptide bond is decisive for the good in vivo effect.

The incorporation of a bactericidal monomer for dental applications is described in J. Dent. Rs. 73(8), 1437–1443 (1994). An antimicrobial effect is observed without release of the active species, although it is not clear whether the effectiveness is derived from a bactericidal or biophobic (antiadhesion) property. The pyridinium compound used is bonded to the polymer skeleton via a hydrophobic spacer (long-chain alkyl residue).

OBJECT AND ACHIEVEMENT

The object of the invention is to provide copolymers which are obtained by copolymerization of monomers having antimicrobial effect and which are suitable for making coatings or shaped articles whose surfaces have biocidal or biophobic properties without releasing toxic compounds. In this way it is intended that subsequent addition of microbiologically active molecules to surfaces by analogy with polymers can be avoided. Another goal is to discover a class of active substances as an alternative to the phenolic compounds, among other purposes to prevent selection of resistant strains by variation or combination of active substances and to close gaps in activity.

It has been found that polymers of the following structure have good antimicrobial properties. The polymers comprise a) 99 to 40 wt % of nonfunctional vinyl-type polymerizable monomers and b) 1 to 60 wt % of functional vinyl-type polymerizable monomers of general formula (I)

$$[V-A_y-HSp]_m-N^{\oplus}(R^1)_{4-(m+t)}-(R^2)_t \cdot X^-  \quad (I)$$

where
V=vinyl, (meth)acroyl, allyl or styryl,
A=a linking unit which is present if necessary, which can be alkyl, aryl, arylalkyl or hydroxyalkyl, and which can also be interrupted by heteroatoms, for example by heteroatoms in urethane, carbonate, ester, amide or ether groups, where y=0 or 1,
HSp=a hydrophilic spacer of general formula $$-(O-CH_2-CH_2)_r- \quad (i)$$

and/or $$-(O-CH_2-CH(CH_3))_s \quad (ii)$$

where r=0 to 40, s=0 to 40 and r+s=2 to 40, as well as
m=1, 2 or 3 and
$R^1$=$CH_3$, ethyl or benzyl
$R^2$=an alkyl residue with 8 to 20 C atoms, where t=1, 2 or 3.
$X^-$=$Cl^-$, $Br^-$, $I^-$ or (alkyl sulfate)$^-$ Monomers a) are preferably chosen mainly from the (meth)acrylic acid esters. Especially preferred are polymers in which monomers b) are (meth)acrylic acid esters of general formula (II)

$$[CH_2=CR^3-CO-(O-CH_2-CHR^4)_n]_m-N^{\oplus}(CH_3)_{4-(m+t)}-(R^2)_t \cdot X^- \quad (II)$$

where
m=1, 2 or 3, n=2 to 40,
$R^2$=an alkyl residue with 8 to 20 C atoms, where t=1, 2 or 3.
$R^3$=H or $CH_3$,
$R^4$=H or $CH_3$
$X^-$=$Cl^-$, $Br^-$, $I^-$ or (alkyl sulfate)$^-$ Although the mechanism of action is not understood, the inventors assume that monomers b), in which a combination of the quaternary ammonium group which contains at least one long-chain alkyl residue and which is bound to a hydrophilic spacer represents the active principle having antimicrobial activity in the polymers according to the invention. This was in no way foreseeable. The use of monomers, especially (meth)acrylic acid esters, which contain vinyl groups and which can undergo radical polymerization to form the antimicrobial polymers opens diverse possibilities of controlling the further polymer properties such as glass transition temperature, minimum film-forming temperature, molecular weight, etc., and so antimicrobial polymers are accessible for a multitude of applications.

WORKING OF THE INVENTION

The polymers according to the invention with antimicrobial properties can be obtained in a way known in itself by radical polymerization of the monomers in the presence of polymerization initiators and if necessary molecular weight regulators.

For this purpose there are used a) nonfunctional vinyl-type polymerizable monomers and b) functional vinyl-type polymerizable monomers of general formula (I). The term functional monomers relates to monomers b) in the sense that the antimicrobial property of the polymers is attributed to their presence.

For the present purpose, an antimicrobial property is understood as a germ-reducing or germ-killing action which occurs when the polymer and germs come into contact with one another in the presence of water.

Monomers a):

Examples of suitable nonfunctional vinyl-type polymerizable monomers according to a) are acrylate or methacrylate compounds, allyl compounds, styrenes, maleic acid, maleic anhydride or other vinyl compounds, such as vinyl esters, etc.

Monomers a) preferably comprise mainly (meth)acrylate compounds, or in other words such compounds account for at least 90% relative to the total quantity of monomers a). Of course, relatively small proportions such as up to 10% of other monomers a) can also be included. Preferred are alkyl (meth)acrylates with 1 to 20 C atoms in the alkyl residue, hydroxy (meth)acrylates or even (meth)acrylate compounds with acid or amide functions. Examples are methyl methacrylate, methyl acrylate, ethyl acrylate, butyl acrylate, ethyl methacrylate, propyl methacrylate, butyl methacrylate, cyclohexyl methacrylate, hydroxyethyl (meth)acrylate, acrylic acid, methacrylic acid, acrylamide, methacrylamide. Relatively small proportions of cross-linking compounds such as glycol dimethacrylate or allyl methacrylate can also be included. Preferred monomers are alkyl (meth)acrylates. Especially preferred monomers a) are methyl methacrylate and butyl acrylate.

Monomers b):

Functional vinyl-type polymerizable monomers according to b) have the general structure of formula (I)

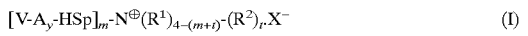
$$[V-A_y-HSp]_m-N^{\oplus}(R^1)_{4-(m+t)}-(R^2)_t \cdot X^- \quad (I)$$

where

V=vinyl, (meth)acroyl, allyl or styryl; (meth)acryloyl is preferred

A=a linking unit which is present if necessary, which can be alkyl, aryl, arylalkyl or hydroxyalkyl, and which can also be interrupted by heteroatoms, for example by heteroatoms in urethane, carbonate, ester, amide or ether groups, where y=0 or 1, although y=0 is preferred. Examples of A are:

2-hydroxypropoxy, (2'-hydroxypropoxyphenyl)(2'-hydroxy-3-oxyphenyl)propane (from bisphenol A diglycidyl ether), 7,7,9-trimethyl-4,13-dioxo-3,14-dioxa-5,12-diazatetradecyl (from HMDI), 6-ketohexyloxy, 6-ketohexylamino, etc.

HSp=a hydrophilic spacer of general formula

$$—(O—CH_2—CH_2)_r— \quad (i)$$

and/or

$$—(O—CH_2—CH(CH_3))_s \quad (ii)$$

where r=0 to 40, s=0 to 40 and r+s=2 to 40

(i) or (ii) is preferred, especially preferred with r=2 to 10 or s=2 to 10, less preferred, but also possible, is (i) and (ii) in mixed or block sequence, m=1, 2 or 3, preferably 1 or 2 and $R^1$=CH$_3$, ethyl or benzyl, preferably CH$_3$ (if a plurality of $R^1$ residues are present they can be the same or different)

$R^2$=an unbranched alkyl residue with 8 to 20, preferably 12 to 18, especially preferably 12 or 14 C atoms, where t=1, 2 or 3, preferably 1 or 2, $X^-$=Cl$^-$, Br$^-$, I$^-$ or (alkyl sulfate)$^-$ (preferred alkyl sulfates are CH$_3$CH$_2$OSO$_3^-$ and CH$_3$OSO$_3$)$^-$; Cl$^-$ is preferred.

Preferred for monomers b) are (meth)acrylic acid esters of general formula (II)

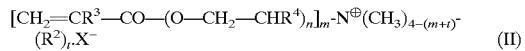
$$[CH_2{=}CR^3{-}CO{-}(O{-}CH_2{-}CHR^4)_n]_m{-}N^{\oplus}(CH_3)_{4-(m+t)}{-}(R^2)_t \cdot X^- \quad (II)$$

where m=1, 2 or 3, preferably 1 or 2, n=2 to 40, preferably 2 to 10, if m>1, n can be the same or different in the individual residues.

$R^2$=an alkyl residue with 8 to 20, preferably 12 to 18, especially preferably 12 or 14

C atoms, where t=1, 2 or 3, preferably 1 or 2

$R^3$=H or CH$_3$, preferably CH$_3$ $R^4$=H or CH$_3$, preferably H $X^-$=Cl$^-$, Br$^-$, I$^-$ or (alkyl sulfate)$^-$, preferably Cl$^-$.

Preferred monomers b) can have general formula (III).

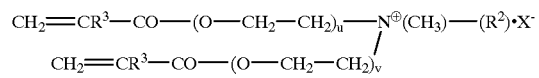

$$\begin{array}{l} CH_2{=}CR^3{-}CO{-}(O{-}CH_2{-}CH_2)_u \\ CH_2{=}CR^3{-}CO{-}(O{-}CH_2{-}CH_2)_v \end{array}\!\!\!\!\!\!\rangle N^{\oplus}(CH_3){-}(R^2)\cdot X^- \quad (III)$$

where u+v=6 to 20, preferably 10

$R^2$=an alkyl residue with 8 to 20, preferably 12 C atoms $R^3$=H or CH$_3$, preferably CH$_3$ $X^-$=Cl$^-$, Br$^-$, I$^-$ or (alkyl sulfate)$^-$, preferably Cl$^-$.

An example of a preferred monomer b) is the compound laurylamine-x-10EO dimethacrylate quat (quat A) according to formula (IV)

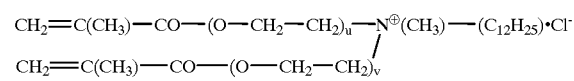

$$\begin{array}{l} CH_2{=}C(CH_3){-}CO{-}(O{-}CH_2{-}CH_2)_u \\ CH_2{=}C(CH_3){-}CO{-}(O{-}CH_2{-}CH_2)_v \end{array}\!\!\!\!\!\!\rangle N^{\oplus}(CH_3){-}(C_{12}H_{25})\cdot Cl^- \quad (IV)$$

where u+v=10 (statistical distribution around the mean value u, v=5)

Preferably monomers b) have general formula (V)

$$CH_2{=}CR^3{-}CO{-}(O{-}CH_2{-}CH_2)_w{-}N^{\oplus}(CH_3)_2{-}R^2 \cdot X^- \quad (V)$$

where w=2 to 40

$R^2$=an alkyl residue with 8 to 20, preferably 14 C atoms, $R^3$=H or CH$_3$, preferably CH$_3$ $X^-$=Cl$^-$, Br$^-$, I$^-$ or (alkyl sulfate), preferably Cl$^-$.

A further preferred monomer b) is the compound 2-(2'-methacroylethoxy)ethyl-dimethyltetradecylammonium chloride (quat B) according to formula (VI)

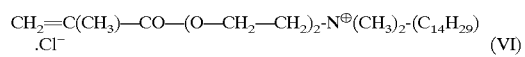
$$CH_2{=}C(CH_3){-}CO{-}(O{-}CH_2{-}CH_2)_2{-}N^{\oplus}(CH_3)_2{-}(C_{14}H_{29}) \cdot Cl^- \quad (VI)$$

Monomers a) are compounds which have long been known and are accessible by standard synthesis techniques. Monomers b) are accessible by synthesis.

General Description of the Synthesis:

Monomers b) are prepared starting from ethoxylated amines by transesterification or esterification with (meth) acrylic acid or (meth)acrylic acid esters followed by quaternization with an alkyl chloride or dialkyl sulfate. As catalysts for the transesterification and esterification there can be used, as in the prior art, acids such as sulfuric acid and para-toluenesulfonic acid, basic catalysts such as calcium hydroxide, calcium oxide, lithium hydroxide, lithium amide or the like, tin catalysts such as dibutyltin oxide and dioctyltin oxide, and metal acid esters such as tetraisobutyl titanate and similar compounds. For process stabilization there are added standard stabilizers such as hydroquinone, hydroquinone monomethyl ether, 4-methyl-2,6-di-tert-butylphenol, phenothiazine or similar compounds as well as combinations thereof. The reaction is advantageously carried out under azeotropic distillation of the resulting water of reaction and low-boiling alcohol.

An alternative preparation route is reaction of the ethoxylated amine as well as of the hydroxyalkyl methacrylate with diisocyanates or diglycidyl ethers of diols such as bisphenol A, followed by quaternization.

Quaternization is performed using alkyl chlorides or dialkyl sulfates in pure form or in solvents. In some cases a reaction in the autoclave (under pressure) is advantageous. The use of (meth)acrylic acid or esters thereof for transesterification or esterification of quaternary ammonium compounds having hydroxy functions is also conceivable.

General description of the synthesis of laurylamine-x-10EO dimethacrylate quat (quat A) and 2-(2'-methacroylethoxy)ethyldimethyltetradecylammonium chloride (quat B):

The advantageously used monomers b), especially quat A (according to formula IV) and quat B (according to formula VI) are synthesized via the methacrylate esters of the corresponding ethoxylated tertiary amines, which are obtained by transesterification with methyl methacrylate and isopropyl titanate. Quaternization is performed advantageously in the autoclave in order to reach higher temperatures. Quaternization with fatty alkyl chlorides is performed preferably in pure substance or with polar solvents, especially preferably with alcohols.

Antimicrobial Polymers Comprising Monomers a) and b)

The polymers according to the invention with antimicrobial properties can be obtained in a way known in itself by radical polymerization of the monomers in the presence of polymerization initiators and if necessary molecular weight regulators.

For this purpose there are used a) nonfunctional vinyl-type polymerizable monomers and b) functional vinyl-type polymerizable monomers of general formula (I). The term functional monomers relates to monomers b) in the sense that the antimicrobial property of the polymers is attributed to their presence.

Antimicrobial properties are understood as an inhibiting effect on the growth of microorganisms, especially bacteria or yeast fungi, or even a germ-reducing effect. Such an effect can be determined by several methods familiar to those skilled in the art. An example of a suitable method is that of the placed drop according to Nurdin, Helary and Sauvet ("Biocidal Polymers Active by Contact. II. Biological Evaluation of Polyurethane Coatings with Pendant Quaternary Ammonium Salts", J. Appl. Pol. Sci. 50, 663–670, 1993). Therein 100 µl of a cell suspension containing approximately 10,000 bacterial cells such as *Klebsiella pneumoniae* is placed on a patch of the polymer to be tested and incubated for a specified time such as 3 hours. Thereafter the drop containing the cell suspension is removed and the number of colony-forming units compared with a control sample is determined. An example of a suitable test to check whether the antimicrobial effect is due to the polymer itself or to diffusing substances such as residual monomers contained in the polymer is one in which polymer patches are placed on a nutrient-medium slide inoculated with bacteria. If diffusing antimicrobial substances are present, they can be manifested by the development of a suppression halo, or in other words a clear zone around the polymer patch, in which bacterial growth is inhibited. Other appropriate test techniques are published in, for example, European Patent Application A 641805.

Monomers a) can be present in proportions of 40 to 99 wt %, preferably 70 to 99, especially preferably 80 to 99, especially 85 to 95 wt %. Monomers b) are present in proportions of 1 to 60 wt %, preferably 1 to 30 wt %, especially preferably 1 to 20 wt % and especially 5 to 15 wt %.

The polymer according to the invention can contain, for example, 30 to 70 wt %, preferably 50 to 60 wt % of methyl methacrylate and 70 to 30 wt %, preferably 35 to 45 wt % of butyl acrylate as monomers a) as well as 1 to 20, preferably 5 to 15, especially 8 to 12 wt % of laurylamine-x-10EO dimethacrylate quat (quat A) or 2-(2'-methacroylethoxy)ethyldimethyltetradecylammonium chloride (q uat B) as monomer b).

The Structure of the Polymers

Monomers a) as a rule are not critical, as long as they do not neutralize the antimicrobial effect of monomers b) on the polymer surface. The choice of monomers a) is therefore guided primarily by the intended purpose and the desired material characteristics of the polymer. If hard, mechanically resistant shaped articles are to be made, the glass transition temperature of the polymers, or the softening temperature in the case of polymers with crystalline fractions, is generally far above room temperature, or in other words between 80 and 150° C., for example. Decorative or functional coatings such as paints are frequently based on polymers with glass transition temperatures in the range of 0 to 100° C. The more flexible the coating must be, in general the lower the glass transition temperature is. Adhesive coatings for application as pressure-sensitive adhesives usually have glass transition temperatures well below 0° C. They are soft and extremely tacky at room temperature. The polymers can be cross-linked if desired, provided this is not detrimental to the antimicrobial action. The polymers according to the invention have glass transition temperatures in the range of from −60° C. to 150° C. Preferred values are 0° C. to 60° C. The glass transition temperature Tg can be found, for example, in literature sources such as Brandrup and E. H. Immergut, "Polymer Handbook", Interscience 1996, pp. III-61 to III-63, or "Plastics Handbook", Volume IX, R. Vieweg and F. Esser, eds., Carl-Hanser-Verlag, Munich 1975, pp. 333 to 339, and T. G. Fox in "Bull. Am. Physics Soc.", Vol. 1 (3), p. 123 (1956).

Even the form of application or processing of the polymer can be a factor in the glass transition temperature to be obtained. The person skilled in the art is aware, for example, that the choice of monomers in the case of application as an aqueous dispersion must ensure that the minimum film-forming temperatures (MFT) of the dispersion, determined per DIN 53787, must not exceed the drying temperature. In general, the MFT will lie between 0 and 60° C.

The choice of monomers a) is therefore made in a manner known in itself. The person skilled in the art knows how to combine monomers whose homopolymers have high or low glass transition temperatures ("hardening" or "softening" monomers) in order to obtain the desired material characteristics. In the preferred embodiment, the polymer according to the invention is not water-soluble and at most is water-swellable to a limited extent.

Monomers a) therefore comprise more than 70% of monomers whose water solubility at room temperature is less than 30 g/l, especially less than 20 g/l. The proportion of such monomers is preferably more than 90%, especially preferably more than 95%. Examples are simple unsaturated monomers such as styrene, ethylene, propylene, vinyl chloride, vinylidene chloride, butadiene, vinyl and allyl esters and ethers such as vinyl acetate, esters of maleic, fumaric and itaconic acids, esters and substituted amides of methacrylic and acrylic acids as well as methacrylonitrile and acrylonitrile.

Especially preferred are the esters of methacrylic and acrylic acids, possibly in combination with styrene, substituted amides of (meth)acrylic acid and (meth)acrylonitrile. Only some representative examples will be cited from the broad selection: $C_1$ to $C_{20}$ alkyl esters of (meth)acrylic acid, especially methyl, ethyl, propyl, butyl (meth)acrylate, cyclohexyl (meth)acrylate, benzyl (meth)acrylate, isobornyl (meth)acrylate and short-chain alkylglycol (meth)acrylates such as ethoxyethyl or butoxyethyl methacrylate or ethyltriglycol methacrylate.

Other than the singly unsaturated monomers, polyunsaturated monomers can also be added in more or less large proportions depending on intended purpose, form of application or manufacturing process. The person skilled in the art is aware of the cases in which he must limit the proportion of such monomers, which can already lead to cross-linking of the polymers during polymerization. An example is solution polymerization, in which proportions smaller than 1% can already lead to cross-linking and thus to gelling of the mixture. On the other hand, for application of a coating comprising monomers followed by curing on the substrate surface, for example by UV irradiation., almost arbitrarily high proportions of polyunsaturated monomers can be used.

Examples of such monomers are ethylene glycol di(meth)acrylate, triethylene glycol di(meth)acrylate, butanediol di(meth)acrylate, hexanediol di(meth)acrylate, trimethylolpropane tri(meth)acrylate, allyl (meth)acrylate, methylenebismethacrylamide, methylenebisacrylamide, divinylbenzene and triallyl cyanurate. Of course, it would be limiting for the content of polyunsaturated monomers if the antimicrobial action were to be impaired by, for example, restricted mobility of the cross-linked polymer chains.

In addition to the monomers with low water solubility, there can be provided limited proportions of monomers whose water solubility at room temperature is higher than 30 g/l, especially higher than 20 g/l. The proportion must be limited to less than 30% of monomers a), and preferably it should be below 10%, especially below 5%. The copolymerization of minor proportions of such monomers to obtain specified characteristics is known. Examples worth mentioning here are the improvement of adhesion to certain substrates, the increase in stability of disperse systems, the improvement of pigmentability or colorability, or the increase in resistance to chemicals by subsequent cross-linking of the polymers. Examples of such monomers are polymerizable carboxylic acids such as (meth)acrylic acid, maleic acid and itaconic acid, polymerizable phosphonic or sulfonic acids such as 1-(meth)acrylamido-2-methylpropanesulfonic acid, hydroxyalkyl (meth)acrylates, glycerol monomethacrylate, glycidyl methacrylate, (meth)acrylamide, N-methylol methacrylamide and ethers thereof, maleic acid, alkoxypolyalkylene glycol (meth)acrylates, dimethylaminoethyl (meth)acrylate, dimethylaminopropyl (meth)acrylamide, unsaturated ethyleneurea derivatives such as N-(2-methacryloyloxyethyl)ethyleneurea, N-vinylpyrrolidone, N-vinylimidazole and saponified vinyl acetate.

Polymerization

In principle, all appropriately used polymerization processes are suitable for synthesizing the polymers (see, for example, H. Rauch-Puntigam, Th. Voelker, Acrylic and methacrylic compounds, Springer Verlag 1967, or Encyclopedia of Polymer Science and Engineering, Vol. 13, pp. 708 ff., John Wiley & Sons, 1988). As a rule, radical polymerization using the standard radical initiators will be chosen. Examples of processes include solution, emulsion, suspension, precipitation and bulk polymerization. A substantial factor for the choice of synthesis process is the form of the application in which the polymer will be used or the nature and manner of subsequent processing/forming. Because of the amphiphilic character and the cationic charge of monomers b), however, it is possible in the individual case that solubility problems or incompatibilities will be encountered which influence the choice of polymerization process or which necessitate some adaptation of the polymerization conditions to be employed.

The person skilled in the art usually can anticipate such problems or is capable of establishing suitable polymerization conditions by preliminary experiments. For example, it may be advisable, in the case of emulsion polymerization, to do without the anionic surfactants that are normally used, in order to avoid incompatibilities with monomers b), and instead to manage with nonionic or cationic surfactants or to work entirely without surfactants. The use of copolymerizable surfactants or general stabilizing units such as alkoxyethylpolyethylene glycol (meth)acrylates is also possible.

In the case of bulk polymerization there may exist the possibility, when monomers a) are extremely hydrophobic, that monomers b) will be too poorly soluble, in which case solution or emulsion polymerization, for example, would be preferred.

It is also possible to apply and cure the monomer mixture as such on a substrate to be coated. This is a well known procedure. In this case polymerization can be initiated by thermal decomposition of initiators or by redox reactions. In most cases, however, curing is achieved by irradiation, especially UV irradiation, using photoinitiators.

The molecular weight of the polymers is not critical to the antimicrobial action. In general, it will be adjusted such that requirements of processability and material characteristics are met. In most cases, the molecular weight lies between 20,000 and 500,000. In this connection, solution polymers and polymers intended for thermoplastic processing tend to be in the lower half of this range, for example around 100,000, whereas emulsion polymers usually have higher molecular weights and tend to be in the upper half of this range. The molecular weight $M_W$ can be determined by, for example, gel permeation chromatography or a light scattering method (see, for example, H. F. Mark et al., Encyclopedia of Polymer Science and Engineering, 2nd Ed., Vol. 10, pp. 1 ff., J. Wiley, 1989). In practice, viscosity measurements are usually preferred.

Of course, lower or higher molecular weights are also possible, up to infinitely high molecular weights in cross-linked systems. The desired molecular weight can be adjusted in ways known in themselves, for example by molecular-weight regulators such as mercaptans, by the initiator or monomer concentrations or by the polymerization temperature.

In selecting monomers a) and b), it is important to consider their copolymerization behavior. The copolymerization behavior is characterized by copolymerization parameters of monomer pairs (see Encyclopedia of Polymer Science and Engineering, Vol. 13, pp. 708 ff., John Wiley & Sons, 1988).

In order to ensure uniform copolymerization of all monomers, it is advantageous to avoid combinations whose copolymerization parameters differ greatly from each other. On the other hand, the person skilled in the art is also aware of methods for forcing copolymerization within certain limits even in the case of unfavorable copolymerization parameters, for example by starting with only part of the preferably copolymerizable partners and introducing the rest to keep up with consumption in the course of polymerization. It is also conceivable that nonuniform copolymerization of the monomers may even be desired, in order to achieve special effects by the heterogeneous polymer composition.

Preferred combinations of monomers a) and b), however, are those for which uniform copolymerization can be expected or which make it unlikely that a considerable part of the monomers will not be incorporated into the copolymer. The copolymerization behavior of the most important monomers a) is known (see J. Brandrup, E. H. Immergut, Polymer Handbook, Third Ed., John Wiley & Sons, 1989). The copolymerization parameters of monomers b) have not been determined by the inventors. It can be assumed, however, that the nature of the double bond substantially determines the copolymerization behavior, and so monomers b) containing a methacryloyl group have copolymerization behavior similar to that of the known methacrylates. Monomers b) with a methacryloyl or acryloyl group are therefore particularly suitable for combination with methacrylates and acrylates of group a) as well as with styrene. Monomers with vinyl double bonds such as vinyl chloride do not exhibit a strong tendency toward copolymerization with methacrylates or acrylates. If such monomers are to be copolymerized with monomers b), it is advantageous, on the basis of knowledge of the copolymerization parameters, for a vinyl ester group, for example, to be chosen as unsaturated group V. Similarly, a person skilled in the art can select further combinations of monomers a) and b) from which advantageous copolymerization behavior can be expected.

Use and Advantageous Characteristics of the Polymers

The copolymers are preferably water-insoluble and at the most have limited swellability in water. They are suitable for the synthesis of coatings and shaped articles in which microbial growth is undesirable and must be avoided. Included herein are coats such as paints for ships, paints for exterior walls, floor coverings or wood glazes, self-adhering coatings, coatings of schedules and shower curtains, finishes for textiles such as woven or nonwoven fabrics, for example for hygiene applications or for filters. Examples of shaped articles would include door handles, railings, toilet or kitchen surfaces, materials for water-conveying parts such as pipes, seals, valves, diaphragms. Textile fibers or yarns can also be made from copolymers having structures according to the invention. In the ideal case, the antimicrobial surface inhibits the growth of microorganisms in the medium adjoining the surface, so that preservative packaging of easily spoiled aqueous goods is also possible without the need for addition of toxic or unsafe substances or of release thereof from the surface.

EXAMPLES

Example 1

Synthesis of Quat A a) Preparation of the dimethacrylate of ethoxylated laurylamine (laurylamine×10EO): 160.5 g of ethoxylated laurylamine (Marlazin L10) is dried by means of cyclohexane in the moisture separator. After distillative removal of the entraining agent, 52 mg of hydroquinone monomethyl ether, 52 mg of phenothiazine, 130 mg of N,N'-diphenyl-p-phenylenediamine and 100 g of methyl methacrylate (MMA) are added and the mixture is dried once again by azeotropic distillation. After addition of another 15 ml of MMA, 1.0 g of tetraisopropyl titanate is added at 80° C. The mixture is heated to boiling and methanol/MMA distilled off. The reaction is ended after 9 hours. The catalyst is precipitated by addition of dilute sulfuric acid and, after neutralization with aqueous sodium carbonate solution, is filtered under pressure. Excess MMA is removed in the rotary evaporator. The yield was 177.6 g; the structure was confirmed by NMR.

b) Preparation of laurylamine-x-10EO dimethacrylate quat (quat A) 85.0 g of dimethacrylate of ethoxylated laurylamine, 45.8 g of acetone, 43 mg of N,N'-diphenyl-p-phenylenediamine and 2 mg of 4-hydroxy-2,2,6,6-tetramethylpiperidinooxyl are introduced into the teflon insert of the autoclave. 4.5 g of chloromethane is introduced under pressure. Stirring is performed for 24 hours at 90° C. During this time the pressure decreases (4 to 5 bar). After cooling to room temperature, the autoclave is opened. There is obtained 118.6 g of clear, brown-colored acetone solution (66 wt %). The structure was confirmed by NMR.

Example 2

Synthesis of 2-(2'-methacroylethoxy)ethyldimethyltetradecylammonium chloride (quat B)

25.0 g of 2-[2-(dimethylamino)ethoxy]ethyl methacrylate, 33.6 ml of 1-chlorotetradecane, 22.8 ml of ethanol, 50 mg of potassium iodide and 12 mg of hydroquinone monomethyl ether are heated for 24 hours with stirring at 105° C. in the autoclave. The pressure rises to about 2 bar. After cooling to room temperature, the autoclave was opened. The quat B is obtained as 75% ethanolic solution. The structure is confirmed by NMR.

Example 3

Preparation of the Copolymer with Quat A 13.3 g of MMA, 10.65 g of butyl acrylate, 4.07 g of quat A solution (66% in acetone, 10 wt % of quat A relative to the mixture of monomers), 0.132 g of 2,2'-azobis-(isobutyronitrile) (AIBN) and 0.1 ml of 2-ethylhexyl thioglycolate are mixed and introduced into a glass chamber (16×16 cm glass plate, 1.5 mm spacer cord) and purged of air bubbles. The chambers are sealed with cement and secured with clamps. Polymerization is carried out for 23 hours at 50° C. in the drying cabinet. After removal of the clamps, the product is heat-treated for 1 hour at 75° C. and 2 hours at 90° C.

Clear, transparent polymers with slightly brownish coloration were obtained (glass transition temperature: 7° C.).

Example 4

Preparation of the Copolymer with Quat B by Emulsion Polvmerization

To 30 g of water there are added 6.89 g of MMA, 5.27 g of butyl acrylate as well as 2.92 g of quat B (as 43% solution) and 0.09 g of 2-ethylhexyl thioglycolate. The mixture is emulsified at 70° C. and a stirring speed of 500 rpm. Then the reaction is initiated at a stirring speed of 250 rpm, using 0.084 g of 2,2'-azobis(2-aminopropane) dihydrochloride (dissolved in 0.1 g of water). After a reaction time of one hour, another 0.042 g of initiator (dissolved in 0.5 g of water) is added to the dispersion, which is then stirred for a further 30 minutes at 70° C. Thereafter the mixture is cooled to room temperature and the dispersion filtered over an ND 70 metal sieve.

Residual monomer content: 296 ppm methyl methacrylate (MMA), 96 ppm butyl acrylate
Solids content: 29.7%
Particle size: 130 nm (no coagulate)

The emulsion was cast on a glass plate bordered with silicone and was dried overnight at 50° C. to obtain a clear, transparent film. Glass transition temperature: 36° C.

Example 5
Preparation of a Comparison Polymer without Functional Monomer b)

Example 3 is repeated, with the difference that a mixture of 22.0 g of MMA, 18.0 g of butyl acrylate, 0.16 g of AIBN and 0.12 g of ethylhexyl thioglycolate is used.

Example 6
Testing of the Polymers from Example 3 and 5 for Bactericidal Properties The polymer films from Example 3 and 5 were stored for 24 hours in water, during which period the water was replaced after 8 hours. The films were then dried in air. The bactericidal action of these polymer films toward the test organisms *Staphylococcus aureus* and *Bacillus cereus* was tested as follows: Each test organism was inoculated with 5 ml of standard I bouillon in an Erlenmeyer flask and incubated as a standard culture for 16 hours at 370° C. The mixture was then diluted by a factor of 1:10000. Strips (5 cm×1 cm) of the polymer films to be examined were coated with 8 ml of this diluted mixture in sterile test tubes. Live germ counts (LGC/g) were then determined immediately and after 2, 4 and 20 hours.

The test tubes were shaken during incubation. The result is summarized in the following table.

|  | Live germ counts (LGC/g) | | | |
| --- | --- | --- | --- | --- |
|  | *Staphylococcus aureus* (ATCC 6538) | | *Bacillus cereus* (ATCC 2) | |
| Incubation time | Polymer from Example 3 | Comparison polymer (Example 5) | Polymer from Example 3 | Comparison polymer (Example 5) |
| none | >10$^5$ | 1.2 × 10$^5$ | >10$^5$ | 6.5 × 10$^3$ |
| 2 hours | 4.2 × 10$^4$ | 3.8 × 10$^4$ | 3.5 × 10$^3$ | 4.5 × 10$^3$ |
| 4 hours | 2.9 × 10$^4$ | 7.1 × 10$^4$ | 1.3 × 10$^3$ | 8.7 × 10$^2$ |
| 20 hours | <10$^1$ | 7.3 × 10$^3$ | <10$^1$ | >10$^6$ |

Example 7
Antimicrobial Properties of the Polymers from Examile 3 and 4 a) Contact inhibition of *Klebsiella pneumoniae* DSM 798 by polymer 4A from Example 3.

The polymer film of polymer 4A from Example 3 was stored in water for 24 hours, the water being replaced after 8 hours. The film was then dried in air.

*K. pneumoniae* DSM 798 (DSM=German Microorganism Collection) was cultured overnight in YPG whole medium (1% yeast extract, 1% peptone and 1% glucose) at 35° C. The cells were collected by centrifuging and taken up in PBS (0.05 M phosphate buffer solution, pH 7.2, 0.9% NaCl) and the cell count adjusted to 10$^5$/ml. 100 μl of the suspension was placed on a patch of the water-treated polymer film of polymer 4A from Example 3. After a contact time of 3 hours in an atmosphere saturated with water vapor, the drop was removed and diluted in 2 ml of saline. The contact area was washed 3 times with saline. 100 μl aliquots were plated on YPG agar. After 18 hours at 37° C., the grown colonies were counted. A patch of polystyrene was used as control polymer. In a parallel experiment, a control test for substances capable of diffusing was performed on YPG agar which had been inoculated with 10$^5$ *K. pneumoniae* germs. No suppression zones were observed. The result is presented in the following table.

| Polymer | Germ count per plate |
| --- | --- |
| Polymer 4A (according to the invention) | 0 |
| Polystyrene (control) | 3000 | b) Selectively inhibiting action of the polymer from Example 4

The contact inhibition test described hereinabove was performed with the polymer from Example 4 (quat B as the comonomer) and four bacterial strains as well as the yeast *Candida tropicalis*. The films obtained were stored in water for 24 hours (the water being changed several times) and tested after they had been dried in air. The lethality is reported in %. Surprisingly, selective inactivation of the yeast strain was observed, but no action was found for the bacterial strains.

| Germ | Lethality in % |
| --- | --- |
| *E. coli* K12 ATCC 23716 | 0 |
| *K. pneumoniae* DSM 798 | 0 |
| *S. aureus*\* | 0 |
| *S. epidermidis* ATCC 12228 | 0 |
| *C. tropicalis* CBS 6318 | 70 |

\* = isolated by Gelsenkirchen Hygiene Institute from an infected central venous catheter Example 8
Example of use of a Polymer A polyamide film strip measuring about 8×2 cm was immersed for half of its length into the dispersion from Example 4 and then dried for 1 hour at 70° C. The strip was water-treated for 18 hours and then dried in air at room temperature.

The strip coated for half of its length with the dispersion was now completely immersed in a cell suspension of *Staphylococcus aureus* (isolated by Gelsenkirchen Hygiene Institute from an infected central venous catheter). Thereafter the strip was dried briefly in air and then placed on dilute nutrient agar and cultured overnight at 370° C.

Result: Compared with 4 *Staphylococcus aureus* colonies on the half of the polyamide strip coated with the dispersion, several hundred grew on the uncoated half.

What is claimed is:
1. Polymers with antimicrobial properties, comprising:
   a) 99 to 40% by weight of a nonfunctional polymerizable monomer having a terminal ethylenically unsaturated group; and
   b) 1 to 60% by weight of a functional polymerizable monomer having a terminal ethylenically unsaturated group of general formula (I)

$$[V-A_y-HSp]_m-N^{\oplus}(R^1)_{4-(m+t)}-(R^2)_t \cdot X^- \qquad (I)$$

wherein
V=vinyl, (meth)acroyl, allyl or styryl;

A=a linking unit selected from the group consisting of an alkyl group, an aryl group, an arylalkyl group or a hydroxyalkyl group, a urethane group, a carbonate group, an ester group, an amide group and an ether group;
where y=0 or 1;
Hsp=a hydrophilic spacer of general formula
(i) $-(O-CH_2-CH_2)_r-$ and/or
(ii) $-(O-CH_2-CH(CH_3))_s$
where r=0 to 40, s=0 to 40 and r+s=2 to 40; and
wherein
m=1, 2 or 3;
$R^1=CH_3$, ethyl or benzyl;
$R^2$=an alkyl residue with 8 to 20 C atoms, where t=1, 2 or 3; and
$X^-=Cl^-$, $Br^-$, $I^-$ or (alkyl sulfate)$^-$.

2. The polymer according to claim 1, wherein monomer b) is a (meth)acrylic acid ester of general formula (II)

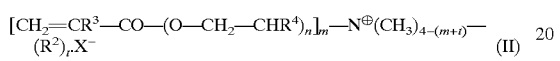
(II)

wherein
m=1, 2 or 3, n=2 to 40;
$R^2$=an alkyl residue with 8 to 20 C atoms, where t=1, 2 or 3;
$R^3$=H or $CH_3$;
$R^4$=H or $CH_3$; and
$X^-=Cl^-$, $Br^-$, $I^-$ or (alkyl sulfate)$^-$.

3. The polymer according to claim 1, wherein monomer b) is a (meth)acrylic acid ester of general formula (III)

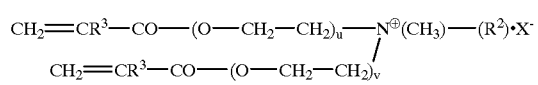
(III)

wherein
u+v=6 to 20;
$R^2$=an alkyl residue with 8 to 20 C atoms;
$R^3$=H or $CH_3$; and
$X^-=Cl^-$, $Br^-$, $I^-$ or (alkyl sulfate)$^-$.

4. The polymer according to claim 1, wherein monomer b) comprises quat A according to formula (IV)

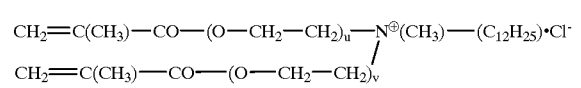
(IV)

wherein u+v=10.

5. The polymer according to claim 1, wherein monomer b) comprises a (meth)acrylic acid ester of general formula (V)

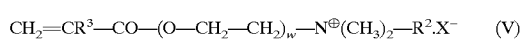
(V)

wherein
w=2 to 40;
$R^2$=an alkyl residue with 8 to 20 C atoms;
$R^3$=H or $CH_3$; and
$X^-=Cl^-$, $Br^-$, $I^-$ or (alkyl sulfate)$^-$.

6. The polymer according to claim 5, wherein monomer b) comprises quat B of formula (VI)

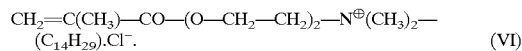
(VI)

7. A plastic or plastic coating, comprising:
the polymer according to claim 1 having an antimicrobial surface.

8. A (meth)acrylate monomer according to formula (II)

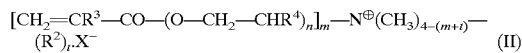
(II)

wherein
m=1, 2 or 3;
n=2 to 40;
$R^2$=an alkyl residue with 8 to 20 C atoms, where t=1, 2 or 3;
$R^3$=H or $CH_3$;
$R^4$=H or $CH_3$; and
$X^-=Cl^-$, $Br^-$, $I^-$ or (alkyl sulfate)$^-$.

9. The monomer according to claim 8, wherein said monomer has formula (III)

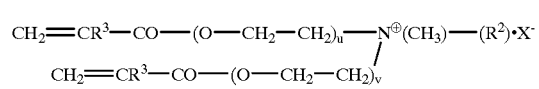
(III)

wherein
u+v=6 to 20;
$R^2$=an alkyl residue with 8 to 20 C atoms;
$R^3$=H or $CH_3$; and
$X^-=Cl^-$, $Br^-$, $I^-$ or (alkyl sulfate)$^-$.

10. The monomer according to claim 8, wherein said monomer has formula (IV)

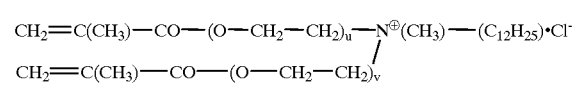
(IV)

wherein u+v=10.

11. The monomer according to claim 8, wherein said monomer has formula (V)

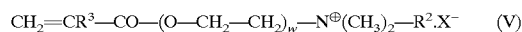
(V)

wherein
w=2 to 40;
$R^2$=an alkyl residue with 8 to 20 C atoms;
$R^3$=H or $CH_3$; and
$X^-=Cl^-$, $Br^-$, $I^-$ or (alkyl sulfate)$^-$.

12. The monomer according to claim 11, wherein said monomer has formula (VI)

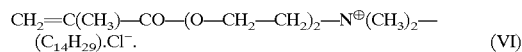
(VI)

13. A process for synthesis of an antimicrobial polymer, comprising:
radical polymerizing of 99 to 40% by weight of a non-functional polymerizable monomer having a terminal ethylenically unsaturated group and 1 to 60% by weight of a (meth)acrylate monomer according to claim 8.

* * * * *